United States Patent
Upmeier et al.

(10) Patent No.: US 11,320,423 B2
(45) Date of Patent: May 3, 2022

(54) METHOD FOR REDUCTION OF INTERFERENCES IN IMMUNOASSAYS

(71) Applicant: Roche Diagnostics Operations, Inc., Indianapolis, IN (US)

(72) Inventors: Barbara Upmeier, Iffeldorf (DE); Toralf Zarnt, Penzberg (DE); Dieter Roessler, Kirchseeon (DE); Johannes Polz, Murnau (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/995,572

(22) Filed: Jun. 1, 2018

(65) Prior Publication Data

US 2018/0348211 A1 Dec. 6, 2018

Related U.S. Application Data

(63) Continuation of application No. PCT/EP2016/079170, filed on Nov. 30, 2016.

(30) Foreign Application Priority Data

Dec. 1, 2015 (EP) .................... 15197192

(51) Int. Cl.
| | | |
|---|---|---|
| *G01N 31/00* | (2006.01) | |
| *G01N 33/53* | (2006.01) | |
| *G01N 33/541* | (2006.01) | |
| *G01N 33/543* | (2006.01) | |
| *G01N 21/64* | (2006.01) | |
| *G01N 21/78* | (2006.01) | |
| *G01N 33/531* | (2006.01) | |
| *G01N 33/538* | (2006.01) | |
| *G01N 33/569* | (2006.01) | |
| *G01N 33/576* | (2006.01) | |

(52) U.S. Cl.
CPC .......... *G01N 33/541* (2013.01); *G01N 21/64* (2013.01); *G01N 21/78* (2013.01); *G01N 33/531* (2013.01); *G01N 33/5306* (2013.01); *G01N 33/538* (2013.01); *G01N 33/54306* (2013.01); *G01N 33/54393* (2013.01); *G01N 33/56994* (2013.01); *G01N 33/5761* (2013.01); *G01N 33/5768* (2013.01)

(58) Field of Classification Search
None
See application file for complete search history.

(56) References Cited

U.S. PATENT DOCUMENTS

| | | |
|---|---|---|
| 5,888,745 A | 3/1999 | Eckert et al. |
| 2007/0059682 A1 | 3/2007 | Aberl et al. |

FOREIGN PATENT DOCUMENTS

| | | |
|---|---|---|
| CN | 1629309 A | 6/2005 |
| JP | 2010-172324 A | 8/2010 |
| WO | 1995/023800 A1 | 9/1995 |
| WO | 1998/023955 A2 | 6/1998 |
| WO | 1998/034109 A1 | 8/1998 |
| WO | 2007/133988 A1 | 11/2007 |
| WO | 2008/061684 A1 | 5/2008 |
| WO | 2008/137885 A1 | 11/2008 |
| WO | 2009/111729 A1 | 9/2009 |
| WO | 2009/125316 A2 | 10/2009 |
| WO | 2010/072384 A1 | 7/2010 |
| WO | 2011/137165 A1 | 11/2011 |
| WO | 2012/022682 A1 | 2/2012 |
| WO | 2013/132338 A2 | 9/2013 |
| WO | 2014/144325 A1 | 9/2014 |
| WO | 2016/097116 A1 | 6/2016 |

OTHER PUBLICATIONS

Park and Kricks-Interferences in Immunoassay, The Immunoassay Handbook, 2013, pp. 403-416. (Year: 2013).*
Liu et al. Diagnosis of toxoplasmosis and typing of Toxoplasma gondii. Parasites & Vectors, May 28, 2015, 8:292, pp. 1 of 14. (Year: 2015).*
Ando, Takao et al., Non-specific Activities against Ruthenium Crosslinker as a New Cause of Assay Interference in an Electrochemiluminescent Immunoasay, Internal Medicine, 2007, pp. 1225-1229.
DeForge, Laura E. et al., Evaluation of heterophilic antibody blocking agents in reducing false positive interference in immunoassays for IL-17AA, IL-17FF, and IL-17AF, Journal of Immunological Methods, 2010, pp. 70-81, vol. 362.
Gessl, Alois et al., Anti-ruthenium antibodies mimic macro-TSH in electrochemiluminescent immunoassay, Clinical Chemistry and Laboratory Medicine, 2014, pp. 1589-1594, vol. 52, No. 11.
International Search Report dated Jan. 31, 2017, in Application No. PCT/EP2016/079170, 4 pp.
Köhler, G. and Milstein, C., Continuous cultures of fused cells secreting antibody of predefined specificity, Nature, 1975, pp. 495-497, vol. 256.
Park, Jason Y. and Kricka, Larry J., Interferences in Immunoassay, The Immunoassay Handbook, 2013, pp. 403-416, Elsevier Ltd.
Roche Diagnostics GmbH, Product Information FT4 II Free thyroxine, 2013, 4 pp., Version 2.0 English.

(Continued)

*Primary Examiner* — Lisa V Cook
(74) *Attorney, Agent, or Firm* — Stinson LLP

(57) ABSTRACT

Disclosed is an immunoassay method for detecting an analyte such as an antigen or an antibody in an isolated sample suspected to contain the analyte by incubating the sample with a plurality of binding partners, one of which carries a detectable label, wherein a label-specific binding partner is added that does not carry a label but binds to the detectable label. The method is applicable for a large variety of analytes and has proven particularly useful for analyte antibodies of the IgG and IgM class present in samples due to infections by pathogens. Also disclosed is a reagent kit useful for the method comprising at least two analyte-specific binding partners one of which carries a detectable label and a label-specific binding partner that binds to said detectable label but itself does not carry a detectable label.

15 Claims, 3 Drawing Sheets

(56) References Cited

OTHER PUBLICATIONS

Roche Diagnostics GmbH, Product Information, Toxo IgG, IgG antibodies to Toxoplasma gondii, 2013, 5 pp., Version 11.0 English.
Roche Diagnostics GmbH, Product Information, Toxo IgM, IgM antibodies to Toxoplasma gondii, 2015, 5 pp., Version 8.0 English.
Sapin, Rémy et al., Efficacy of a new blocker against anti-ruthenium antibody interference in the Elecsys free triiodothyronine assay, Clinical Chemistry and Laboratory Medicine, 2007, pp. 416-418, vol. 45, No. 3.
Scantibodies Laboratory, Inc., State-of-the-Art Blocking of False Positives, 60 pp.
Qin, Xiaochun. et al., Detecting specific IgM antibodies using IgM antibody capture method, Foreign Medicine (Microbiology), 1988, pp. 249-252, English Abstract.
Xu, Q. et al., Progress in pathology of glioma, Journal of Practical Oncology, 2004, pp. 458-462, English Abstract, vol. 19, No. 6.

\* cited by examiner

METHOD FOR REDUCTION OF INTERFERENCES IN IMMUNOASSAYS

CROSS REFERENCE TO RELATED APPLICATIONS

This application is a continuation of International Application No. PCT/EP2016/079170 filed Nov. 30, 2016, which claims priority to European Application No. 15197192.6 filed Dec. 1, 2015, the disclosures of which are hereby incorporated in their entirety.

FIELD OF THE INVENTION

The invention concerns a method for reduction of interferences in immunoassays that are caused by interfering factors that bind to a detectable label that is used for direct or indirect detection of an analyte. More specifically the invention concerns an immunoassay method for detecting an analyte, in an embodiment an antibody or an antigen in an isolated sample by incubating said sample with a plurality of binding partners, one of which carries a detectable label, wherein a label-specific binding partner is added that does not carry a label but binds to said detectable label.

BACKGROUND OF THE INVENTION

Methods for eliminating interferences in immunodiagnostic assays are well-known in the art and have been described in detail. For review, see for example Park and Kricka (The Immunoassay Handbook Elsevier Ltd. 2013, Chapter 5.3, pages 403-415). In particular solid-phase-based immunoassays, so-called heterogeneous assays, are subject to various interferences that can lead to false-positive or false-negative assay results, high background signal, decreased assay sensitivity and dynamics, lack of reagent stability and shortened shelf-life of these reagents. Non-specific interference is often caused by nonspecific binding of assay components to solid phase material independently of the presence of an analyte. Another source of interference is the presence of rheumatoid factors, anti-IgM antibodies or anti-animal-antibodies (heterophilic antibodies) such as human anti-mouse antibodies (HAMA).

Another frequent source for interference is the signal-generating component that is used in an immunoassay. Known signal-generating compounds are for example enzymes or labels emitting light based on fluorescent, colorimetric, chemiluminescent or electrochemiluminescent principles. In particular for electrochemiluminescent compounds interference due to non-specific binding to the signal-generating compound has been described in prior art (Ando et al. Intern Med 2007, 46(15): 1225-1229; Sapin et al., Clin Chem Lab Med 2007; 45(3):416-418).

In order to avoid interferences based on the signal-generating component often an excess amount of carrier protein linked to said signal-generating component is added to an immunoassay mixture. As a result the interfering compound or factor binds to said signal-generating component attached to the free carrier protein. In case this measure is not sufficient to eliminate the interference also a substance can be added to the immunoassay mixture that is structurally similar to the real signal-generating component but does not provide any signal by its own. As a consequence, interfering factors present in the sample bind to the excess similar compound in a quantitative way and do not bind to the real target, i.e. the signal-generating compound. Thus the interference can be suppressed. Such a procedure has been described for example in U.S. Pat. No. 5,888,745 and its equivalent DE 195 19 973. In these documents a method for determining an analyte is disclosed wherein an analyte-specific binding substance is attached to a metal-containing complex capable of providing a luminescence signal. In said method a second metal-containing complex that is structurally related to the first metal-containing complex but does not bind to the analyte is added to the sample to be investigated. This second metal-containing complex helps in reducing the quenching of the first metal-containing complex's signal.

However, although measures for eliminating interferences are available immunoassays tend to show interference that cannot be eliminated by simply adding an additional amount of competing compounds similar to the signal-generating compound to the assay admixture.

The problem to be solved can therefore be seen in increasing the specificity of an immunoassay based on emission of a detectable signal.

When we added a compound to an immunoassay that binds to the label itself that caused the problem the interference was reduced. This was surprising because our expectation was that the label itself would be masked and shielded so that no or only an insufficient detectable light signal could be generated anymore by the shielded label.

SUMMARY OF THE INVENTION

The invention is based on the finding that a signal-generating compound or detectable label, in particular a light-generating label that is attached to a binding partner, is masked and shielded from its environment by adding a label-specific binding partner.

The invention concerns an immunoassay method for detecting an analyte, in an embodiment an antigen or an antibody in an isolated sample suspected to contain said analyte by incubating said sample with a plurality of binding partners, one of which carries a detectable label, wherein a label-specific binding partner is added that does not carry a label but binds to said detectable label.

The method is applicable for a large variety of analytes and has proven particularly useful for analyte antibodies of the IgG and IgM class present in samples due to infections by pathogens.

The invention further concerns a reagent kit useful for said method comprising a plurality of binding partners, at least one of which binds to the analyte, and one of which carries a detectable label and one of which is a label-specific binding partner that binds to said detectable label but itself does not carry a detectable label.

In addition, the invention covers the use of a label-specific binding partner that does not carry a detectable label in an in vitro diagnostic test for eliminating interferences caused by anti-label antibodies present in a sample.

b) as is a) but the first binding partner is indirectly labeled by adding an additional labeled binding partner that binds the first binding partner;

c) double-antigen sandwich format (DAGS) for detecting antibodies; first and second binding partners both bind the analyte. The first binding partner carries a detectable label itself or it can also be indirectly labeled by adding an additional binding partner that carries a label and that binds to the first binding partner as shown in b).

Figure 2:
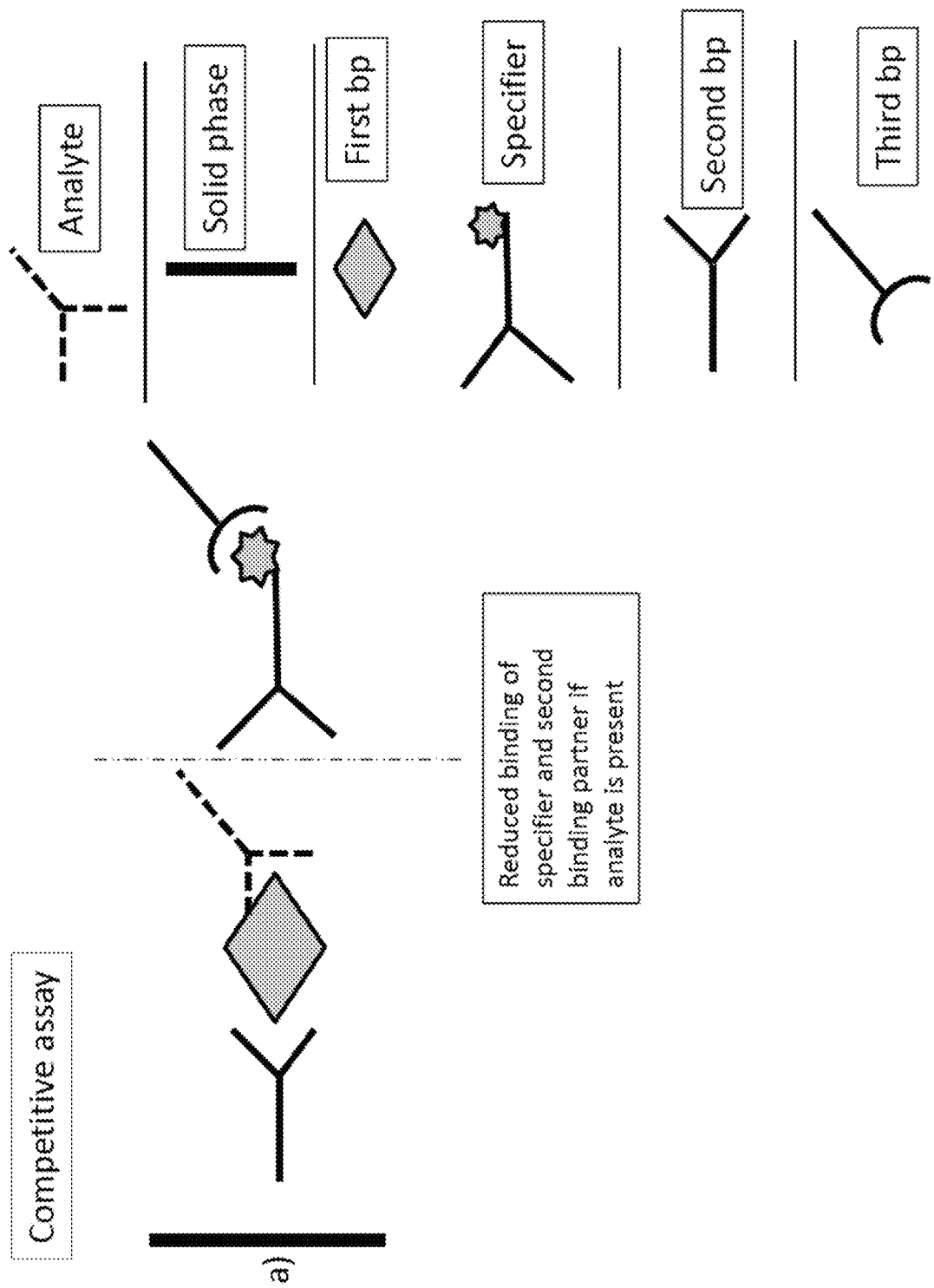

FIG. 2 (embodiment a) shows a schematic drawing of a competitive assay format. In competitive formats the relation between a detected signal and presence of analyte is reversed, i.e. for embodiment a) in the absence of the analyte the specifier is able to bind to the analyte-specific binding partner and provides a measurable signal. On the other hand, in the presence of analyte binding of the specifier to the analyte-specific binding partner is suppressed due to competition with the analyte. Also the binding of the second binding partner to the analyte-specific binding partner is reduced if the analyte is present. As a consequence no or lower signal shows that the analyte is present in the investigated sample.

Figure 3:
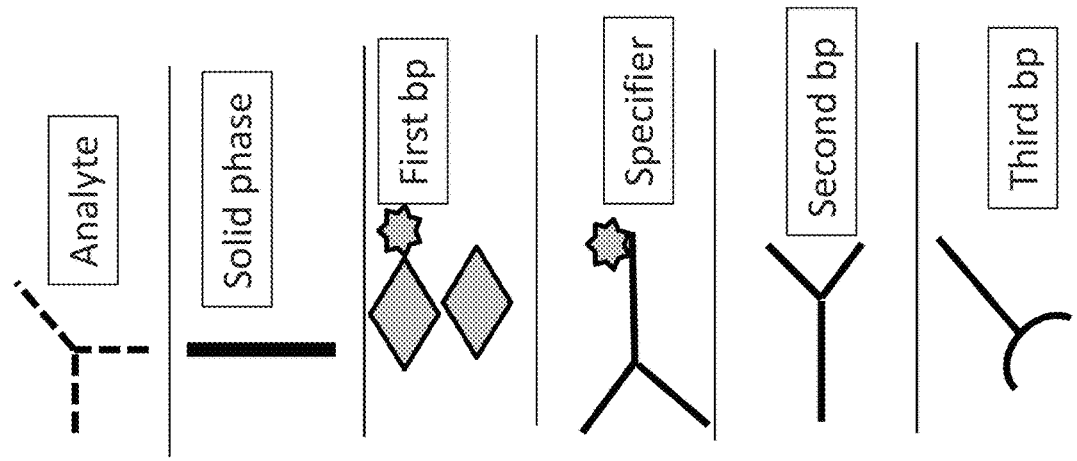
Figure 3:
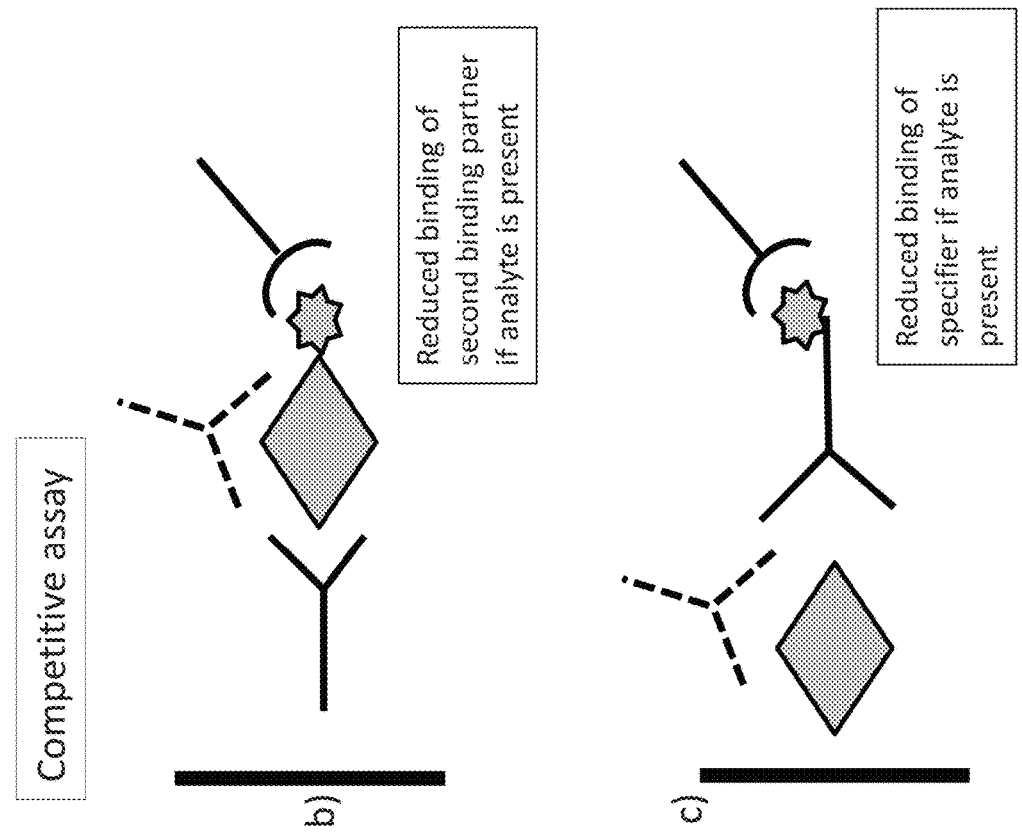

FIG. 3 shows two additional embodiments b) and c) of a competitive assay format according to the invention. Also here the relation between a detected signal and presence of analyte is reversed, i.e. in the absence of the analyte the detectable signal emitted by the label is high, i.e. higher than in the presence of the analyte where the measurable signal is decreased.

b) In this embodiment the first binding partner carries a label and no specifier is used. The second binding partner competes with the analyte for binding to the labeled first binding partner.

c) In this embodiment the first binding partner does not carry a label and is capable of being bound to a solid phase. No second binding partner is used for attachment of the immunocomplex to the solid phase. The specifier carries a label. The analyte competes with the specifier for binding to the first binding partner.

In both embodiments b) and c) the third binding partner is added which binds to the label that is carried by either the first binding partner (b)) or the specifier (c)).

BRIEF DESCRIPTION OF THE TABLES

Table 1 shows the results of a Toxoplasma gondii IgM immunoassay as described in Examples 2 and 3.

Table 2 shows the results of a Toxoplasma IgM immunoassay with varying concentrations of a label-specific binding partner as anti-interference component (see Example 3).

Table 3 shows the results of an Anti-hepatitis B core immunoassay with optimized concentration of a label-specific binding partner as anti-interference component. For details refer to Example 4. Table 4 shows the elimination of interference by addition of a label-specific binding partner in an immunoassay (non-competitive sandwich format) for detection of the thyroid hormone TSH. Details are described in Example 5.

DETAILED DESCRIPTION OF THE INVENTION

The invention concerns an immunoassay method for detecting an analyte in an isolated sample suspected to contain said analyte by incubating said sample with a plurality of binding partners, one of which carries a detectable label, wherein a label-specific binding partner is added that does not carry a label itself but binds to said detectable label. An immunoassay is a biochemical test that detects the presence and/or the quantity of a biological molecule present in biological fluids by using binding partners composed of amino acids; these binding partners are derived from antibodies and/or antigens.

Different formats and variants of immunoassays are widely known in the art, such as homogeneous and heterogeneous immunoassays. In homogeneous immunoassays reagents and samples are mixed and directly measured for example by turbidimetric methods.

This invention concerns heterogeneous immunoassays. Heterogeneous immunoassays are run in multiple steps where reagents, in an embodiment binding partners, in another embodiment an analyte-specific binding partner that carries a detectable label, are added to a sample to be investigated. These assays are called "heterogeneous" because two phases are needed, a liquid and a solid phase. Before, during or after completion of the immunoreaction in solution between the analyte and a specific binding partner—making up an immunocomplex—said immunocomplex is attached to a solid phase, in an embodiment a microtiter plate latex or polystyrol beads. This results in two "heterogeneous" phases, a liquid and a solid phase. After separation of liquid and solid phases the signal emitted from a label attached to an analyte-specific binding partner is detected in either the solid phase or the liquid phase or in both phases.

The immunoassay can be carried out either in a competitive or a non-competitive format. In the competitive format, the analyte contained in a sample competes with a labeled binding partner which is similar or identical to the analyte for binding to a capture compound, which is frequently an antibody, or, in case the presence of antibodies to e.g. a pathogenic agent to be tested in a serum sample, an antigen of said pathogenic agent.

Figure 1:
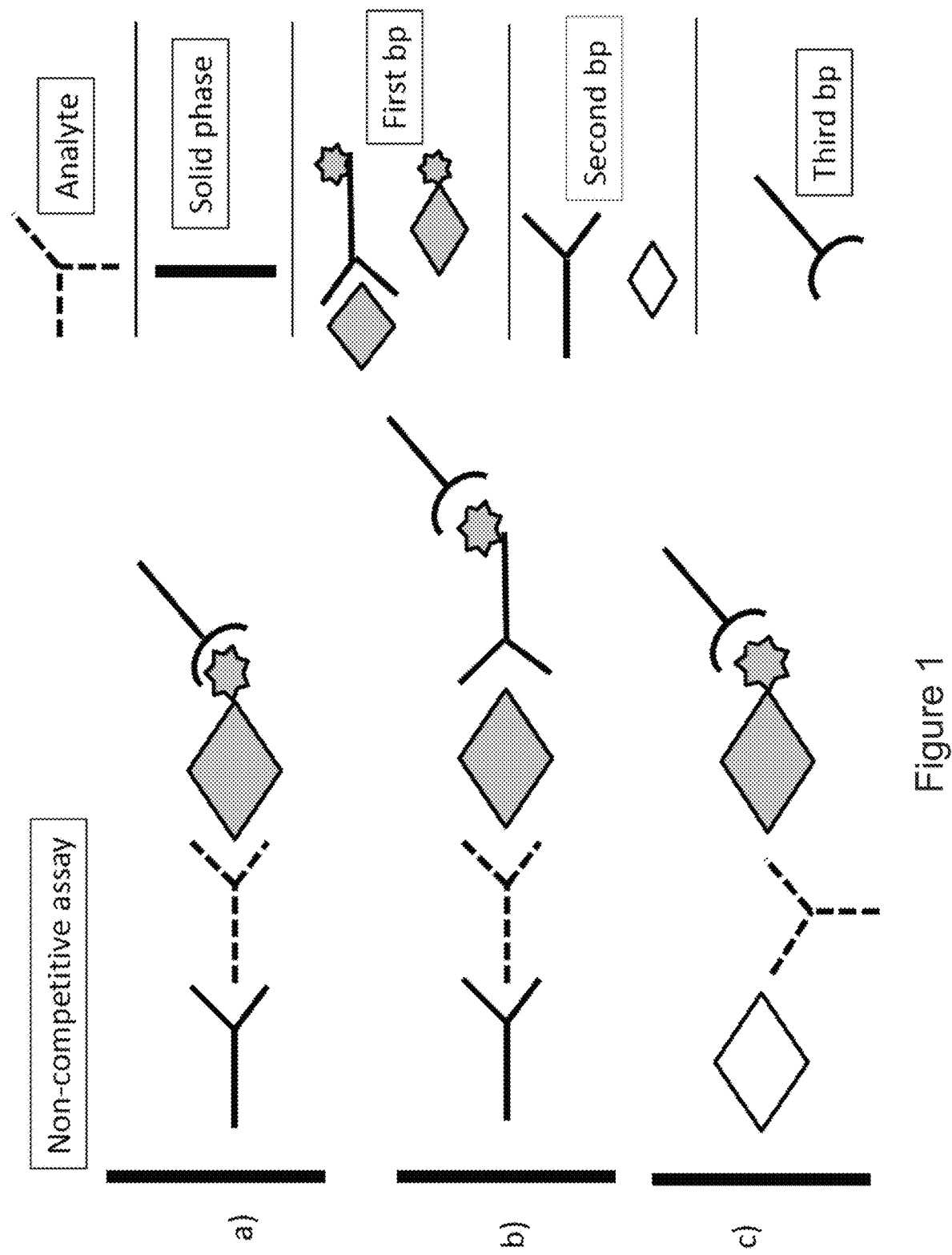
FIG. 1 shows a schematic drawing of a non-competitive assay principle. In this format the detected signal is directly proportional to the amount of the analyte, i.e. a small concentration of analyte results in a low measured signal whereas a high concentration of analyte leads to an increased signal. If no analyte is present no signal above a predetermined background or cut-off value can be detected. a) format for detecting a specific class of antibodies, in an embodiment IgM antibodies (μ capture); the first binding partner is an analyte-specific antigen that carries a detectable label.

In an embodiment of the invention the immunoassay method has got a non-competitive format (for illustration of various specific formats, see FIG. 1). In this case the analyte is detected by contacting the analyte with a compound binding to the analyte, i.e. an analyte-specific binding partner. This analyte-specific binding partner either carries a detectable label itself or is the target of another binding partner carrying a detectable label. The term "carries a detectable label" includes both a directly attached label and a label that is conferred indirectly by adding another labeled binding partner that binds to the analyte-specific binding partner (for illustration see e.g. FIG. 1 b)). Thus, in non-competitive immunoassays, the amount of analyte is determined by determining the amount of complexes formed between the analyte and a detector compound carrying a label. Well-known non-competitive immunoassay formats are the classic sandwich format (analyte captured between two analyte-specific antibodies), the double-antigen sandwich format (analyte is an antibody captured between two specific antigens) and the μ-capture format wherein IgM-antibodies are captured by an antibody specific for human-IgM antibodies. In this so-called μ-capture format usually the analyte IgM-antibody is detected using a labeled antigen that binds to the μ-captured IgM analyte.

In more detail, said immunoassay method carried out in a non-competitive format comprises the following steps:
  a. incubating said sample with
    i. a first binding partner that binds to the analyte and that carries a detectable label ii. a second binding partner that is capable of being bound to a solid phase and that binds to the analyte iii. a third binding partner that binds to detectable label of said first binding partner, wherein said third binding partner does not carry a label b. forming an immunoreaction admixture by admixing said sample with said first, second and third binding partners c. maintaining said immunoreaction admixture for a time period sufficient for allowing said analyte if present in the body fluid sample to immunoreact with said first and second binding partners to form an immunoreaction product; and allowing said third binding partner to immunoreact with said detectable label of said first binding partner d. detecting the presence and/or the concentration of any of said immunoreaction product.

An embodiment of the non-competitive format is further illustrated in FIG. 1. According to the invention a plurality of binding partners is applied, at least one of which is an analyte-specific binding partner.

A binding partner is a biological molecule based on a polypeptide, composed of amino acids. The term "composed of amino acids" means that the main components of a binding partner are amino acids forming a polypeptide. It includes also polypeptides that have a backbone made of amino acids wherein one or more residues are modified by sugar moieties or lipid residues. However, binding partners composed of nucleic acids or carbohydrates as main compound are not included. In an embodiment, a binding partner contains modifications by sugar residues. In an embodiment, a binding partner comprises chemical linker molecules in order to attach additional moieties, in an embodiment labels or compounds used for attaching said binding partner to a solid phase. An example of this is biotin that can be attached to a binding partner by a chemical linker based on e.g. polyethylenglycol units.

An analyte-specific binding partner is a biological molecule based on a polypeptide composed of amino acids that binds to the analyte. The features detailed above for a binding partner also apply to an analyte-specific binding partner. The analyte-specific binding partner is applied as first binding partner. Such an analyte specific binding partner can be an antibody or a fragment thereof binding to the analyte. An antibody or antibody fragment is particularly useful as analyte specific binding partner if the analyte is an antigen. If the analyte is an antibody then typically an antigen binding to the analyte antibody is applied as analyte-specific binding partner. In a non-competitive assay format the first binding partner (analyte-specific binding partner) carries a label.

For illustration, in an assay for detecting IgM antibodies against Toxoplasma gondii the antigen Toxo p30 antigen is applied as an analyte specific binding partner that binds to Toxoplasma gondii antibodies present in the sample. The Toxo p30 antigen carries a detectable label. An embodiment of the invention is an immunoassay method according to the non-competitive format described above wherein the analyte is an antibody against Toxoplasma gondii.

For further illustration, in an immunoassay for detecting a hormone as analyte, in an embodiment the glycoprotein thyroid-stimulating hormone (TSH), a TSH-specific antibody is applied as analyte-specific binding partner that binds to the antigen analyte TSH in the sample to be investigated. Said TSH-specific antibody carries a detectable label. The analyte forms a sandwich with a second TSH-specific antibody that is capable of being bound to a solid phase. An embodiment of the invention is an immunoassay method according to the non-competitive format wherein the analyte is a hormone, in an embodiment a glycoprotein hormone, in yet another embodiment TSH.

The designations i., ii., and iii. are merely descriptive terms and shall not be understood in such a way that a timewise or stepwise order is associated with the addition of the individual binding partners to the immunoreaction admixture. For example, the third binding partner (see step iii) does not need to be added last but could also be added first or all binding partners listed under i., ii., and iii. can be added simultaneously etc.

Binding of the first and second binding partners to the analyte as well as the binding of the third binding partner to the label (that is carried by the first binding partner) take place in a specific manner that can also be described as exclusive binding with high affinity. This means that the first binding partner specifically binds to the analyte, the second binding partner also specifically binds to the analyte and also the third binding partner specifically binds to the label attached to the first binding partner. This means for example that in an embodiment where the analyte is an IgM molecule against Toxoplasma gondii the first binding partner is an antigen that is recognized by and binds to the analyte IgM, in an embodiment Toxo p30 antigen. In this embodiment the second binding partner that can be bound to a solid phase is an antibody against the Fc part of IgM antibodies (µ-chain). As a result, the second binding partner specifically binds to the Fc-part of IgM-molecules and the first binding partner (Toxo p30 antigen) that carries a label specifically binds to the paratope of the analyte IgM antibody.

The term "specific" or "specific(ally) binding" also indicates that other compounds, typically biomolecules, that are present in a sample do not significantly bind to the analyte, binding partners and the label (summarized as target molecules). This does not exclude binding of other chemical compounds, to regions of the target molecules not involved in interaction with the analyte, binding partners, and the label.

According to the invention a second binding partner is applied that is capable of being bound to a solid phase. This binding partner can be an antibody or a fragment thereof. In a so-called double-antigen sandwich (DAGS) format which can be used for detecting analyte antibodies the second binding partner is an antigen binding to the analyte antibody. This antigen can be bound to a solid phase for example by conjugating the antigen with biotin and attaching it to a streptavidin-coated solid phase.

As explained above, in assays according to the µ-capture format as additional binding partner (second binding partner) an antibody binding to human IgM is applied. This second binding partner binds IgM molecules independently of their antigen-specificity reflected in the IgM analyte's paratope (it would bind to all IgM molecules in the sample). The second binding partner can be bound to a solid phase. Binding mechanisms of biomolecules to a solid phase are well-known in the art, the easiest way being direct coating of proteins to a plastic surface, e.g. to a microtiter plate. In an embodiment the binding to a solid phase takes place via biotin-streptavidin interaction, wherein the second binding partner carries a biotin moiety and the solid phase is coated with streptavidin.

According to the invention a label-specific binding partner is added as third binding partner to an incubation admixture containing the sample to be analyzed and a plurality of binding partners. This label-specific binding partner is a biological molecule based on a polypeptide composed of amino acids that binds to the label applied for detection that is carried by one of the binding partners. The definition of binding partner further above applies also to the label-specific binding partner. In the non-competitive format the label is usually attached directly or indirectly to one of the analyte-specific binding partners. In an embodiment it is attached to the first binding partner. In an embodiment of a competitive assay format (see further below) the label is attached to a specifer that competes with the analyte for binding to the other binding partner present in the incubation admixture.

Preferably, said label-specific binding partner is an antibody or a fragment thereof binding to the label. It is important that the label-specific binding partner itself does not carry a label and does not interact or does not significantly interact with other assay components except for the label. In other words, detection concepts known in the art that are based on a method wherein the label of a specific binding partner is recognized by a label-specific binding partner which itself also carries a label (e.g. the digoxin/digoxigenin and anti-digoxin/digoxigenin antibodies) are not encompassed as those concepts are not applicable for reducing the interference arising from anti-label antibodies.

The exact stoichiometry for the amount of label-specific binding partner acting as third binding partner compared to the amount of label is not critical so that absolute maximal and minimal concentration ranges are not essential to make the invention work. The only condition that needs to be fulfilled is that the assay reagents stay functional.

For comparison and counting of the molar proportions of a third binding partner (label-specific binding partner) one has to determine the actual binding sites that are available for masking the label. This means e.g. that a Fab fragment has got one paratope and therefore counts as one binding site whereas e.g. a complete IgG antibody or $Fab_2$ fragment has got two paratopes (binding sites) and thus counts as two binding sites.

For certain assays it may be helpful to provide an excess of label-specific binding partner (=third binding partner) compared to the molar amount of label. In other assays the situation may be reversed and it may be helpful to add a molar excess of label compared to the amount of label-specific binding partner. For example, in an embodiment of 1:10 (proportion of binding sites of a label-specific binding partner to label) the molar excess of label to be shielded in comparison to the binding sites of a label-specific binding partner is 10-fold, which means that every tenth label molecule could be bound and covered by a binding site of the label-specific binding partner. In another embodiment, the situation would be reversed as e.g. 10:1, i.e. the binding sites of a label-specific binding partner would be present in 10-fold excess. In yet another embodiment the molar the proportions of label-specific binding partner binding sites to label are at least 1:20, in another embodiment 1:10, in another embodiment 1:5, in another embodiment 1:3, in another embodiment 1:2, in another embodiment 1:1.5, in another embodiment 1:1, in another embodiment 2:1, in another embodiment 3:1, in another embodiment 5:1, in another embodiment 10:1, in another embodiment 20:1, in another embodiment 50:1 and in yet another embodiment at least 100:1.

When the label-specific binding partner is added to an immunoassay admixture it binds to the label, thereby covering and shielding the label from interaction with interfering compounds present in the sample. At the same instance and because of its size and three-dimensional structure the label-specific binding partner can sterically also shield or block the linker attached to the label from interaction with interfering sample compounds. As a result also interferences caused by non-specific binding by sample ingredients to a linker sequence can also be avoided. By adding a label-specific binding partner that itself does not carry a label the interfering component, i.e. the label is masked on purpose thereby preventing binding of further anti-label component that might be present in the sample to the label.

If no label-specific binding partner is added then quite often false-positive results can be observed. For example, in an assay format based on the μ capture format these interferences are often caused by the presence of non-specific IgM class antibodies. In an assay design based on the μ-capture format these interfering anti-label-IgMs are captured to the solid phase. Since the anti-label-IgMs also bind to the labeled specific compound the labeled analyte-specific binding binding partner binds to the solid phase although no real analyte is present in the sample. As a result, a false positive signal is observed.

Detectable labels are also widely known to the expert. According to an embodiment of the current invention a detectable label is an enzyme, or a label emitting light, in an embodiment fluorescence, luminescence, chemiluminescence, electrochemiluminescence or radioactivity. In a preferred embodiment the label is an electrochemiluminescent label, in an embodiment Tris(2,2'-bipyridyl)ruthenium(II)-complex (Ru(bpy)). As the interference is caused by the three-dimensional structure of the label molecule that attracts auto-antibodies and similar interfering molecules and not by the signal-emitting mechanism of said label, such as e.g. light or radioactivity, all the above-referenced labels can be used in the current invention.

The term detectable label comprises also a linker sequence that is attached to said label connecting the label with an analyte-specific binding partner. Usually a linker sequence is based on a peptidic backbone of 1-100 natural or synthetic amino acids.

In another embodiment the immunoassay method can be carried out in a competitive format, comprising the following steps:
  a. Incubating said sample with
    i. a first binding partner that binds to the analyte and that does not carry a detectable label
    ii. a specifier which binds to the first binding partner and which competes with the analyte for binding to the first binding partner wherein said specifier carries a detectable label
    iii. a second binding partner that is capable of being bound to a solid phase and that binds to said first binding partner and which competes with said analyte and said specifier for binding to said first binding partner
    iv. a third binding partner that binds to said detectable label of said specifier, wherein said third binding partner does not carry a label
  b. forming an immunoreaction admixture by admixing said sample with said first, second and third binding partners and said specifier
  c. maintaining said immunoreaction admixture for a time period sufficient for allowing said analyte if present in said body fluid sample to compete with said specifier and second binding partner for binding to said first binding partner, and allowing said third binding partner to immunoreact with said detectable label of said specifier, thereby forming an immunoreaction product;
  d. detecting the presence and/or the concentration of any of said immunoreaction product.

An embodiment of the competitive immunoassay format is illustrated in FIG. 2. In a competitive immunoassay format the interference problem can be explained as follows: When no label-specific binding partner according to the invention is present the binding of the interfering compound to the label leads to a reduction of the measured signal. For the interpretation of a signal in a competitive format this means that a reduced signal could be understood and interpreted as a (false) positive result as also competition with a real analyte leads to reduction in signal. In order to avoid this interference a label-specific binding partner according to the invention is added to the immunoassay admixture so that the potential binding sites for an interfering compound are already occupied and blocked. As a consequence the overall signal range is reduced. However and surprisingly, the analyte present in true positive samples still competes with the assay compounds so that this true positive sample can still be reliably detected.

The properties of the plurality of binding partners used in a competitive immunoassay format differ from those used in a non-competitive format in some aspects. The first binding partner that binds to the analyte does not carry a label in said competitive format. The detectable label is attached instead to a specifier that is applied. A specifier binds to the first binding partner and is typically structurally similar to the analyte. Said specifier therefore competes with the analyte for binding to the first binding partner. The second binding partner is capable of being bound to a solid phase, in so far corresponding to the properties of the second binding partner described for the non-competitive format further above. However, in the competitive format the second binding partner binds to the first binding partner (not to the analyte) and competes with the analyte and the specifier for binding to the first binding partner.

The properties of the third binding partner that does not carry a label itself and that binds to the label of the specifier are the same as those for the non-competitive format. The designations i., ii., iii. and iv. are merely descriptive terms and shall not be understood in such a way that a timewise or stepwise order is associated with the addition of the individual binding partners to the immunoreaction admixture. For example, the third binding partner (see step iv) does not need to be added last but could also be added first or all binding partners listed under i., ii., iii. and iv. can be added simultaneously etc.

An example of a competitive immunoassay is an assay for detection of anti-hepatitis B core antibodies, see example 4.

In another embodiment the method for detecting an analyte in an isolated sample can be carried out in a competitive format as illustrated in FIG. 3 (embodiment b), wherein no specifier is added and the first binding partner carries a label (instead of the specifier that is not present in this case). Said method comprises the following steps:
  a. Incubating an isolated sample with
    i. a first binding partner that binds to the analyte that carries a detectable label
    ii. a second binding partner that is capable of being bound to a solid phase and that binds to said first binding partner and which competes with said analyte for binding to said first binding partner
    iii. a third binding partner that binds to said detectable label of said first binding partner wherein said third binding partner does not carry a label
  b. forming an immunoreaction admixture by admixing said sample with said first, second and third binding partners
  c. maintaining said immunoreaction admixture for a time period sufficient for allowing said analyte if present in said body fluid sample to compete with said second binding partner for binding to said first binding partner, and allowing said third binding partner to immunoreact with said detectable label of said first binding partner, thereby forming an immunoreaction product;
  d. detecting the presence and/or the concentration of any of said immunoreaction product.

In yet another embodiment the can be carried out in a competitive format as illustrated in FIG. 3 (embodiment c), wherein no second binding partner is added and the first binding partner is capable of being bound to a solid phase (instead of using a second binding partner that is not present in this case). Said method comprises the following steps:
  a. Incubating an isolated sample with
    i. a first binding partner that binds to the analyte that is capable of being bound to a solid phase and that does not carry a detectable label
    ii. a specifier which binds to the first binding partner and which competes with the analyte for binding to the first binding partner wherein said specifier carries a detectable label
    iii. a third binding partner that binds to said detectable label of said first binding partner wherein said third binding partner does not carry a label
  b. forming an immunoreaction admixture by admixing said sample with said first and second binding partners and said specifier
  c. maintaining said immunoreaction admixture for a time period sufficient for allowing said analyte if present in said body fluid sample to compete with said specifier for binding to said first binding partner, and allowing said third binding partner to immunoreact with said detectable label of said specifier, thereby forming an immunoreaction product;
  d. detecting the presence and/or the concentration of any of said immunoreaction product.

An analyte for both competitive and non-competitive immunoassays can be any chemical or biological molecule that is large enough to be detected by an immunoassay, in an embodiment antigens, antibodies and hormones. Some analytes appear in a sample as a consequence of an infection, an inflammatory, septic, metabolic, cardiac or oncologic event or disease. Other analytes are drugs a patient takes and the concentration of this drug needs to be monitored such as drugs for immunosuppression after organ transplantation (therapeutic drug monitoring). Some analytes, mostly hormones, are determined in a fertility check.

In yet another embodiment the analyte is an enzyme, cytokine, growth factor, hormone, vaccine, antibody and the like. More particularly, an analyte can be a thyroid hormone, in an embodiment triiodothyronine (T3) and its prohormone thyroxine (T4), thyroid-stimulating hormone (TSH) and TSH receptor autoantibodies, erythropoietin, insulin, somatotropin, growth hormone releasing factor, growth factors, in an embodiment platelet derived growth factor, epidermal growth factor, transforming growth factor α, transforming growth factor, epidermal growth factor, fibroblast growth factor, nerve growth factor, insulin-like growth factor I, insulin-like growth factor II, clotting Factor VIII, superoxide dismutase, interferon, γ-interferon, interleukin-1, interleukin-2, interleukin-3, interleukin-4, interleukin-5, interleukin-6, granulocyte colony stimulating factor, multi-lineage colony stimulating factor, granulocyte-macrophage stimulating factor, macrophage colony stimulating factor, T cell growth factor, lymphotoxin and the like. In an embodiment the analyte is a cardiac marker, in an embodiment Troponin T and I, NT-proBNP, BNP as well as sepsis markers.

In an embodiment the analyte is a polypeptide, in an embodiment an antigen or an antibody present in an isolated sample. In an embodiment the analyte is a pathogen and detectable proteins and antigens present due to the infection by said pathogen. The analyte may be derived from any viral, bacterial or protozoic pathogen, which is capable of causing a detectable immune reaction, i.e. a generation of antibodies, particularly IgM antibodies as a result of an infection. For example, the pathogen is selected from the group consisting of i. a Toxoplasma organism, in an embodiment Toxoplasma gondii,
ii. hepatitis viruses, in an embodiment hepatitis A virus (HAV), hepatitis B virus (HBV) and hepatitis C virus (HCV);
iii. herpes viruses, in an embodiment human herpes simplex virus 1 and 2 (HHV1 and HHV2), varicella zoster virus (HHV3), Epstein-Barr virus (HHV4/EBV) or human cytomegalovirus (HHV5) and human herpes viruses 6, 7, and 8;
iv. rubella virus;
v. a retrovirus, in an embodiment HIV 1 and 2 and HTLV 1 and 2;
vi. paramyxoviruses, in an embodiment measles virus and mumps virus;
vii. a Borrelia organism.

In another embodiment the analyte is an antibody of the IgM or IgG class present as a result of an infection by any of the pathogens listed above. In case the analyte is an IgM or IgG antibody the analyte binds to an epitope derived from the pathogen's own structural or non-structural proteins, in an embodiment capsid/core antigen or envelope antigen or soluble antigens present within the pathogen.

In an embodiment the analyte is an antibody of the IgM class present as a reaction to an infection with a pathogen selected from the group consisting of Toxoplasma gondii, cytomegalovirus (CMV), Rubella, hepatitis A and hepatitis B.

All biological liquids known to the person skilled in the art can be used as isolated samples for the described immunoassay method. The samples usually used are bodily liquids like whole blood, blood sera, blood plasma, urine or saliva. As sample any biological liquid isolated from a vertebrate can be used. In an embodiment samples originate from mammalians, in particular from humans.

Yet another aspect of the invention is a reagent kit for detecting of an analyte by an immunoassay comprising a plurality of binding partners, at least one of which binds to the analyte and one of which carries a detectable label and a label-specific binding partner that binds to said detectable label but does not carry a detectable label itself. In an embodiment the analyte-specific binding partner carries said label. An additional subject matter of the invention is a reagent kit for the detection of IgM antibodies against Toxoplasma gondii, comprising a plurality of binding partners one of which is an anti-human IgM antibody that can be bound to a solid phase and one of which is a Toxoplasma gondii specific antigen that carries a detectable label, and a label-specific binding partner that binds to said detectable label but itself does not carry a detectable label.

In addition, the reagent kits defined above contain controls and standard solutions as well as reagents in one or more solutions with the common additives, buffers, salts, detergents etc. as used by the average man skilled in the art along with instructions for use.

A further embodiment of the invention is the use of in a label-specific binding partner that does not carry a detectable label in an in vitro diagnostic test for eliminating interferences caused by anti-label antibodies present in a sample.

The following examples illustrate the invention.

Example 1

Production of Monoclonal Antibodies Against Ruthenium Label

The general procedure for producing monoclonal antibodies is well-known in prior art. The pre-formulated fusion polypeptide immunogen is administered to an experimental animal, such as mouse, rat, rabbit, sheep, or hamster, intraperitoneally at different dosages. Prior to collection of the B-cells a boost immunization is performed. B-cell hybridomas can be obtained according to the method of Koehler and Milstein (Koehler, G. and Milstein, C., Nature 256 (1975) 495-497). The hybridomas obtained are deposited as single clones or cells in the wells of a multi well plate. Primary culture supernatants are tested by ELISA for reactivity against the immunogen.

Monoclonal mouse antibodies with specificity for the electrochemiluminescent label Ruthenium (II) tris-bipyridine N-hydroxysuccinimide were produced by administering mice with the immunogen Ruthenium (II) tris-bipyridine N-hydroxysuccinimide conjugated to keyhole limpet hemocyanin (BPRu-KLH) according to procedures described in prior art. The cells obtained from immunization were analyzed using an ELISA for their specificity for Ruthenium (II) tris-bipyridine N-hydroxysuccinimide.

8-12 weeks old Balb/c mice, respectively, were subjected to repeated intraperitoneal immunizations with 100 µg of immunogen Ruthenium (II) tris-bipyridine N-hydroxysuccinimide conjugated to keyhole limpet hemocyanin (BPRu-KLH). The mice were immunized three times, i.e. also at the time points of 6 weeks and 10 weeks after the initial immunization. The first immunization was performed using complete Freund's adjuvant, the second and third immunizations were done using incomplete Freund's adjuvant. The mice serum titers were tested after 12 weeks by ELISA methods as described in the following. The ELISA was performed on a microplate reader. ELISA plates were coated with the immunogen Ruthenium (II) tris-bipyridine N-hydroxysuccinimide conjugated to keyhole limpet hemocyanin (BPRu-KLH) by applying a solution comprising 0.5 µg antigen per ml. Thereafter free binding sites were blocked by applying a solution comprising 1% RPLA in PBS for one hour at room temperature. The wells were washed three times with a solution comprising 0.9% (w/v) sodium chloride and 0.05% (w/v) (polysorbate 20) TWEEN 20. Mouse serum was diluted 1:50 with PBS and used as sample. The incubation time was one hour at room temperature. The wells were washed three times with a solution comprising 0.9% (w/v) sodium chloride and 0.05% (w/v) (polysorbate 20) TWEEN 20. As detection antibody a polyclonal antibody against the constant domain of the target antibodies conjugated to a peroxidase was used (PAK<M-Fcγ>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) (polysorbate 20) TWEEN 20. Afterwards, the wells were incubated with an ABTS solution for 15 minutes at room temperature. The intensity of the developed color was photometrically determined.

Three days before preparation of spleen cells and fusion with a myeloma cell line, the final booster immunization was performed by i.v. injection of 100 µg of immunogen Ruthenium (II) tris-bipyridine N-hydroxysuccinimide conjugated to keyhole limpet hemocyanin (BPRu-KLH).

ELISA Screening of Hybridoma

Primary culture supernatants were tested by ELISA for reactivity against the immunogen Ruthenium (II) tris-bipyridine N-hydroxysuccinimide conjugated to keyhole limpet hemocyanin (BPRu-KLH) and a blank plate, respectively. ELISA plates were coated with 0.5 µg/ml immunogen Ruthenium (II) tris-bipyridine N-hydroxysuccinimide conjugated to keyhole limpet hemocyanin (BPRu-KLH). Thereafter, free binding sites were blocked by 1% RPLA in PBS for one hour at room temperature. The wells were washed three times with a solution comprising 0.9% (w/v) sodium chloride and 0.05% (w/v) (polysorbate 20) TWEEN 20. Undiluted hybridoma supernatants were used as samples. The incubation time was one hour at room temperature. The wells were washed three times with a solution comprising 0.9% (w/v) sodium chloride and 0.05% (w/v) (polysorbate 20) TWEEN 20. As detection antibody a polyclonal antibody against the constant domain of the target antibodies conjugated to a peroxidase was used (PAK<M-Fcy>S-F(ab')$_2$-POD). The detection antibody was applied at a concentration of 80 ng/ml in PBS comprising 1% (w/v) RSA. The incubation time was one hour at room temperature. The wells were washed three times with a solution comprising 0.9% (w/v) sodium chloride and 0.05% (w/v) (polysorbate 20) TWEEN 20. Afterwards the wells were incubated with an ABTS solution for 15 minutes at room temperature. The intensity of the developed color was determined photometrically at 405 nm. The reference wavelength was 492 nm. Primary hybridoma supernatants showing fast and strong color formation in ELISA upon binding to Ruthenium (II) tris-bipyridine N-hydroxysuccinimide conjugated to keyhole limpet hemocyanin (BPRu-KLH) were selected. Using this procedure Mab<BPRu>M-1 IgG as applied in Examples 3 and 4 was identified.

Example 2

Detection of IgM Antibodies to Toxoplasma gondii

The immunoassay for the in vitro qualitative determination of IgM antibodies to Toxoplasma gondii was carried out according to the manufacturer's instructions on an automated Elecsys® 2010 analyzer (Roche Diagnostics GmbH). Elecsys® is a registered trademark of the Roche group.

Signal detection in Elecsys® 2010 is based on electrochemiluminescence. The biotin-conjugate (i.e. the capture-antigen) is immobilized on the surface of a streptavidin coated magnetic bead whereas the detection-antigen bears a complexed Ruthenium cation (switching between the redox states 2+ and 3+) as the signaling moiety. In the presence of a specific immunoglobulin analyte, the chromogenic ruthenium complex is bridged to the solid phase and emits light at 620 nm after excitation at a platinum electrode. The signal output is in arbitrary light units.

The assay is based on the so-called µ-capture principle wherein a sample suspected to contain anti-T. gondii IgM antibodies is incubated with ruthenylated T. gondii-specific recombinant antigen and biotinylated anti-human IgM mouse monoclonal antibody. If T. gondii-specific IgM antibodies are present in said sample the anti-IgM capture these antibodies. After addition of a streptavidin-coated solid phase a removal of excess liquid the electrochemiluminescence signal originating from the ruthenium complex label can be detected.

In detail, the following steps were carried out; total duration of the assay was 18 minutes:
  1st incubation: 10 µL of sample were automatically pre-diluted 1:20 with Diluent Universal. T. gondii-specific recombinant antigen labeled with a ruthenium complex (R1; Ru complex: Tris(2,2'-bipyridyl)ruthenium(II)-complex (Ru(bpy))) was added. Anti-T. gondii IgM antibodies present in the sample reacted with the ruthenium-labeled T. gondii-specific recombinant antigen.
  2nd incubation: Biotinylated monoclonal h-IgM-specific antibodies (R2) and streptavidin-coated microparticles (M) were added. The complex became bound to the solid phase via interaction of biotin and streptavidin.
  The reaction mixture was aspirated into the measuring cell where the microparticles were magnetically captured onto the surface of the electrode. Unbound substances were then removed with ProCell. Application of a voltage to the electrode then induced chemiluminescent emission which was measured by a photomultiplier.
  Results were determined automatically by the software by comparing the electrochemiluminescence signal obtained from the reaction product of the sample with the signal of the cutoff value previously obtained by calibration.

As negative calibrator Cal1 human serum, negative for anti-Toxo IgM, was used. As positive calibrator Cal2 Anti-Toxo IgM (human) approx. 130 U/mL (Roche units) in human serum was applied.

Example 3

Reduction of Interference in an Immunoassay for IgM Antibodies to Toxoplasma gondii Commercially available human serum samples were purchased from in.vent Diagnostica GmbH (Hennigsdorf/Berlin, Germany) and screened for interfering properties. These samples were tested along with in-house false-positive samples as well as with true Toxo IgM and IgG positive samples. Among the Toxo IgM and IgG positive samples we also tested two subgroups of samples, i.e. one group with IgG of high avidity (late infection) and one group with IgG of low avidity (early or primary infection). All samples were tested with Elecsys Toxo IgM (Roche Diagnostics GmbH Germany) according to the procedure described above. As a negative control PC1 [human serum free of anti-Toxo antibodies] was used; as positive control PC2 [Toxo-IgM positive human serum]. A signal to cutoff ratio (S/CO)≤0.8 was regarded as non-reactive (negative); a signal to cutoff ratio (S/CO)≥0.8<1.0 was classified as undetermined and a signal to cutoff ratio (S/CO)≥1.0 was classified as reactive (positive).

Results are shown in Table 1. In the absence of a label-specific binding partner to eliminate interference sera classified as interference samples beginning with "C21" to "SN947 (16)" these samples show up as falsely positive. When a label-specific binding partner (Mab<BPRu>M-1 IgG) is added that binds to the label the overall signal decreases for all samples including real positives. However, the cut-off index remains constant. Real positive samples are still correctly detected as positive. Interestingly and surprisingly the signal for the interference samples goes down to the negative calibration value. In other words, when a label-specific binding partner is added false positives can be avoided resulting in higher assay specificity.

TABLE 1

Toxo IgM - Reduction of interference in Toxo IgM immunoassay

| Sample type | Sample ID | Cut-Off (MV CAL1 * 1 + MV CAL2 * 0.47) S/CO = Counts/Cut-Off | Toxo IgM Lot 165820 Reference 5528 Counts | S/CO | Toxo IgM Lot 165820 Mab<BPRu>M-1 IgG (10 µg/mL in R1) 2706 Counts | S/CO |
|---|---|---|---|---|---|---|
| | CAL1 | | 1128 | 0.204 | 722 | 0.267 |
| | | | 1091 | 0.197 | 755 | 0.279 |
| | CAL2 | | 9392 | 1.70 | 4177 | 1.54 |
| | | | 9408 | 1.70 | 4196 | 1.55 |
| | PC1 (0.00-0.36) | | 1188 | 0.215 | 765 | 0.283 |
| | PC2 (1.06-1.98) | | 8650 | 1.56 | 3807 | 1.41 |
| Toxo IgM positive, Toxo IgG positive, Toxo IgG high avidity | ID 200373 | | 43374 | 7.85 | 19801 | 7.32 |
| | ID 201069 | | 37454 | 6.78 | 11823 | 4.37 |
| | ID 201245 | | 28319 | 5.12 | 12392 | 4.58 |
| | ID 211336 | | 35177 | 6.36 | 17032 | 6.29 |
| | ID 221385 | | 21579 | 3.90 | 9719 | 3.59 |
| Toxo IgM positive, Toxo IgG positive, Toxo IgG low avidity | ID 201172 | | 18809 | 3.40 | 7092 | 2.62 |
| | ID 201331 | | 20762 | 3.76 | 9241 | 3.41 |
| | ID 201864 | | 36905 | 6.68 | 15175 | 5.61 |
| | ID 201959 | | 56196 | 10.2 | 22756 | 8.41 |
| | ID 202687 | | 44421 | 8.04 | 19033 | 7.03 |
| Toxo IgM interference samples (Ruthenium interference), Toxo IgG negative, competitor assay Toxo IgM negative | C21 | | 48916 | 8.85 | 785 | 0.290 |
| | A14 | | 45439 | 8.22 | 808 | 0.299 |
| | A13 | | 35087 | 6.35 | 796 | 0.294 |
| | InventDiagnostica 181636 | | 21103 | 3.82 | 775 | 0.286 |
| | InventDiagnostica 211902 | | 23473 | 4.25 | 995 | 0.367 |
| | SN 856 ID634666 | | 22446 | 4.06 | 978 | 0.361 |
| | C22 | | 17370 | 3.14 | 759 | 0.280 |
| | C13 | | 19189 | 3.47 | 888 | 0.328 |
| | A17 | | 15772 | 2.85 | 742 | 0.274 |
| | C11 | | 16268 | 2.94 | 787 | 0.291 |
| | A21 | | 18187 | 3.29 | 910 | 0.336 |
| | A26 | | 15276 | 2.76 | 787 | 0.291 |
| | SN 854 ID634447 | | 14482 | 2.62 | 823 | 0.304 |
| | C17 | | 23797 | 4.30 | 1404 | 0.519 |
| | B27 | | 12737 | 2.30 | 797 | 0.294 |
| | SN945 (14) | | 12535 | 2.27 | 864 | 0.319 |
| | SN1200 (37) | | 10707 | 1.94 | 808 | 0.298 |
| | B9 | | 9186 | 1.66 | 778 | 0.287 |
| | InventDiagnostica 191161 | | 9131 | 1.65 | 787 | 0.291 |
| | CAL1 | | 1128 | 0.204 | 722 | 0.267 |
| | | | 1091 | 0.197 | 755 | 0.279 |
| | CAL2 | | 9392 | 1.70 | 4177 | 1.54 |
| | | | 9408 | 1.70 | 4196 | 1.55 |
| | PC1 (0.00-0.36) | | 1188 | 0.215 | 765 | 0.283 |
| | PC2 (1.06-1.93) | | 8650 | 1.56 | 3807 | 1.41 |
| Continued: Toxo IgM interference samples (Ruthenium interference), Toxo IgG negative, competitor assay Toxo IgM negative | B24 | | 8892 | 1.61 | 824 | 0.304 |
| | SN938 (7) | | 9576 | 1.73 | 898 | 0.332 |
| | B30 | | 9050 | 1.64 | 851 | 0.314 |
| | A29 | | 8686 | 1.57 | 846 | 0.312 |
| | C8 | | 8689 | 1.57 | 887 | 0.328 |
| | InventDiagnostica 212135 | | 7673 | 1.39 | 786 | 0.291 |
| | InventDiagnostica 210138 | | 7814 | 1.41 | 804 | 0.297 |
| | C23 | | 7458 | 1.35 | 789 | 0.292 |
| | C19 | | 7905 | 1.43 | 839 | 0.310 |
| | SN 858 ID634883 | | 7858 | 1.42 | 837 | 0.309 |
| | InventDiagnostica 210088 | | 6893 | 1.25 | 780 | 0.288 |
| | SN1197 (34) | | 6674 | 1.21 | 757 | 0.280 |
| | B3 | | 8258 | 1.49 | 958 | 0.354 |
| | A16 | | 7747 | 1.40 | 925 | 0.342 |
| | B26 | | 6525 | 1.18 | 820 | 0.303 |
| | Männlich SN 857 ID634670 | | 7823 | 1.42 | 990 | 0.366 |
| | SN1193 (30) | | 6291 | 1.14 | 799 | 0.295 |
| | C24 | | 6387 | 1.16 | 869 | 0.321 |
| | InventDiagnostica 201444 | | 8697 | 1.57 | 1191 | 0.440 |
| | C25 | | 6011 | 1.09 | 856 | 0.316 |
| | InventDiagnostica 202203 | | 5971 | 1.08 | 856 | 0.316 |
| | SN1192 (29) | | 13632 | 2.47 | 2021 | 0.747 |
| | SN1201 (38) | | 8904 | 1.61 | 1330 | 0.491 |
| | SN1203 (40) | | 6998 | 1.27 | 1058 | 0.391 |
| | C9 | | 6070 | 1.10 | 922 | 0.341 |
| | SN 866 ID635887 | | 5887 | 1.07 | 1014 | 0.375 |
| | SN947 (16) | | 9137 | 1.65 | 1783 | 0.659 |

Table 2 shows the results of the interference eliminating effect at different concentrations of the label-specific binding partner. Commercially available native samples and in-house samples that do not contain any T. gondii antibodies were tested for the positive results in an Elecsys Anti-Toxo IgM assay. The reference column shows that all of the eight samples tested provide a positive signal above the cut-off value falsely indicating that these samples contain Toxo-IgM antibodies.

tics GmbH). Elecsys® is a registered trademark of the Roche group. The general detection principle on the analyzer works in an analogous way as described in Example 1 (Anti-Toxo IgM).

In detail, the anti-HBc assay assay works according to the competition principle where the analyte (anti-HBc antibody) competes with biotinylated and ruthenium-labeled antibodies for binding to HBc antigen in the reaction mixture. Total duration of the assay was 27 minutes.

TABLE 2

|  | Toxo IgM Lot# 16582002 - Reference | | Toxo IgM Lot# 16582002 - Mab<BPRu>M-1 IgG (10 µg/mL in R1) | | Toxo IgM Lot# 16582002 Mab<BPRu>M-1 IgG (0.5 µg/mL in R1) | | Toxo IgM Lot# 16582002 Mab<BPRu>M-1 IgG (0.25 µg/mL in R1) | |
|---|---|---|---|---|---|---|---|---|
| Cut-Off (MV CAL1 * 1 + MV CAL2 * 0.47) | 5527.9 | | 2706.2 | | 5119.5 | | 5341.6 | |
|  | MV | COI | MV | COI | MV | COI | MV | COI |
| CAL1 | 1128 | 1110 | 722 | 738 | 1171 | 1105 | 1100 | 1094 |
| CAL1 | 1091 |  | 755 |  | 1039 |  | 1088 |  |
| CAL2 | 9392 | 9400 | 4177 | 4187 | 8521 | 8542 | 9023 | 9038 |
| CAL2 | 9408 |  | 4196 |  | 8563 |  | 9052 |  |
| PC1 | 1188 | 0.21 | 765 | 0.28 | 1059 | 0.21 | 1118 | 0.21 |
| PC2 | 8650 | 1.56 | 3807 | 1.41 | 7537 | 1.47 | 8071 | 1.51 |
| Interference samples: | | | | | | | | |
| InventDiagnostica 181636 | 21103 | 3.82 | 775 | 0.29 | 16506 | 3.22 | 19626 | 3.67 |
| InventDiagnostica 191161 | 9131 | 1.65 | 787 | 0.29 | 6749 | 1.32 | 7674 | 1.44 |
| InventDiagnostica 202203 | 5971 | 1.08 | 856 | 0.32 | 4489 | 0.88 | 5217 | 0.98 |
| InventDiagnostica 201444 | 8697 | 1.57 | 1191 | 0.44 | 6359 | 1.24 | 7627 | 1.43 |
| InventDiagnostica 211902 | 23473 | 4.25 | 995 | 0.37 | 18887 | 3.69 | 21148 | 3.96 |
| InventDiagnostica 210088 | 6893 | 1.25 | 780 | 0.29 | 5525 | 1.08 | 6156 | 1.15 |
| InventDiagnostica 210138 | 7814 | 1.41 | 804 | 0.30 | 6732 | 1.31 | 7456 | 1.40 |
| InventDiagnostica 212135 | 7673 | 1.39 | 786 | 0.29 | 6699 | 1.31 | 7266 | 1.36 |

Increasing amounts (0.25, 0.5 and 10 µg/ml) of an interference-eliminating compound were added to the assay mixture (R1), i.e. in this case an anti-ruthenium complex monoclonal antibody Mab<BPRu>M-1 IgG which binds to the signal-generating ruthenium complex attached to the recombinant Toxo antigen. As expected, the absolute signal intensity is quenched by adding said label-specific binding partner. However, surprisingly when sufficient anti-label-specific binding partner is added the interference can be suppressed providing correct results below the cutoff and below the cut-off index (see column 10 µg/ml in R1). In this example the molar excess or proportion of label specific binding partner (that has two paratopes) compared to the label is about 1:10, i.e. the label is present in about 10-fold access so that every tenth label is covered by a label-specific binding partner.

Even at a concentration of 1 µg/ml in R1, which means that even a smaller proportion of label is shielded, a satisfying elimination of interference can be observed (data not shown). In other words, addition of a label-specific binding partner that binds to a label meant to indicate whether an analyte is present or not suppresses interferences effectively so that false-positive assay results can be avoided. At the same time, a positive control (see row PC1, negative control and PC2, positive control containing Toxo-IgM) still provides correct negative or positive results.

Example 4

Detection of Anti-Hepatitis B Core IgG and IgM Antibodies (Competitive Format)

The immunoassay for the in vitro qualitative determination of IgG and IgM antibodies to hepatitis B core antigen was carried out according to the manufacturer's instructions on an automated Elecsys® 2010 analyzer (Roche Diagnos- 1st incubation: Pretreatment of 40 µL of sample was carried out with a reducing agent (R0)
2nd incubation: After addition of HBcAg recombinant antigen (R1), a complex was formed with anti-HBc antibodies in the sample.
3rd incubation: After addition of biotinylated antibodies and ruthenium complex-labeled antibodies specific for HBcAg (R2; Ru complex: Tris(2,2'-bipyridyl)ruthenium(II)-complex (Ru(bpy)), together with streptavidin-coated microparticles (M), the still-free binding sites on the HBc-antigens became occupied. The entire complex was bound to the solid phase via interaction of biotin and streptavidin.

The reaction mixture was aspirated into the measuring cell where the microparticles were magnetically captured onto the surface of the electrode. Unbound substances were then removed with ProCell. Application of a voltage to the electrode then induced chemiluminescent emission which was measured by a photomultiplier.

Results were determined automatically by the software by comparing the electrochemiluminescence signal obtained from the reaction product of the sample with the signal of the cutoff value previously obtained by calibration.

As negative calibrator Cal1 human serum (not infected by hepatitis B) was used. As positive calibrator Cal2 Anti-HBc (human)>8 WHO IU/mLb) in human serum was used. WHO IU means WHO international units.

Table 3 shows the elimination of interference by addition of a label-specific binding partner in an immunoassay for detection of antibodies against hepatitis B core antigen. This assay is performed in a competitive format which means that high signals and a signal to cut-off ratio of >1.0 indicate a non-reactive (negative) sample whereas a low signal and a signal to cut-off ratio of ≤1.0 are indicative for a reactive (positive) sample.

TABLE 3

| | | A-HBc Lot 170815 Reference 142088 | | A-HBc Lot 170815 10 µg/mL Mab<BPRu>M-1 IgG in R2 32736 | |
|---|---|---|---|---|---|
| | Cut-Off (MV CAL1 * 0.47 + MV CAL2) | Counts | S/CO | Counts | S/CO |
| | S/CO = Counts/Cut-Off | | | | |
| | CAL1 (170815) | 303796 | | 67910 | |
| | | 297730 | | 67174 | |
| | CAL2 (170815) | 737 | | 1003 | |
| | | 722 | | 979 | |
| | PC1 (167128) (1.68-2.62) | 306381 | 2.16 | 68759 | 2.10 |
| | PC2 (167129) (0.31-0.79) | 80039 | 0.563 | 16524 | 0.505 |
| A-HBc interference sample (false-positive) | SE-0064_18 (Trina) | 145231 | 1.02 | 59062 | 1.80 |
| A-HBc negative | 1004 | 252731 | 1.78 | 59684 | 1.82 |
| | 2418 | 243798 | 1.72 | 53067 | 1.62 |
| A-HBc positive | Anti-HBc IgM 60 | 722 | 0.005 | 991 | 0.030 |
| | 2333 | 717 | 0.005 | 993 | 0.030 |

Sample SE-0064_18 (Trina A-HBc negative serum) provides a signal very close to the cut-off with a signal to cut-off value of 1.02. When a label-specific binding partner is added, the sample provides a measuring result (S/CO=1.80) indicating that no anti-HBc antibodies are present in said sample. Also in this case the addition of a label-specific binding partner leads to an increased specificity of the assay.

Example 5

Detection of Thyroid-Stimulating Hormone (TSH, Thyrotropin, Classic Sandwich Format)

The immunoassay for the in vitro quantitative determination of TSH was carried out according to the manufacturer's instructions on an automated Elecsys® cobas analyzer (Roche Diagnostics GmbH). Elecsys® is a registered trademark of the Roche group. The general detection principle on the analyzer works in an analogous way as described in Example 1 (Anti-Toxo IgM).

In detail, the TSH assay works according to the sandwich principle using a reagent R1 comprising a biotinylated monoclonal TSH-specific antibody (R1) and a monoclonal TSH-specific antibody labeled with a ruthenium complex (R2) react to form a sandwich complex. As a first incubation step, 30 µl of sample was incubated with both antibodies for 9 minutes. In the second step, reagent R2, comprising streptavidin-coated microparticles was added and incubated for additional 9 minutes. After that the reaction mixture was aspirated into the measuring cell where the microparticles were magnetically captured onto the surface of the electrode. Application of a voltage to the electrode then induced chemiluminescent emission which was measured by a photomultiplier. Results were determined via a calibration curve which is instrument-specifically generated by 2-point calibration.

For each sample two aliquots were measured. One aliquot was measured in a standard procedure without addition of the interference-reducing binding partner (untreated reference). The second aliquot was incubated with R1 and R2 as the comparison aliquot, however, the R2 reagent (ruthenylated antibody) for the second aliquot additionally contained a label-specific binding partner (here: 20 µg/ml Mab<BPRu>M-1 IgG, specifically binding to the ruthenium complex), a mouse monoclonal antibody binding to the ruthenium label complex.

As can be seen from Table 4, the absolute counts for the calibrators (Cal1 low TSH concentration, Cal 2 higher TSH concentration) decrease for the set-up applying the anti-interference agent compared to the untreated reference. However, a reasonable measurement range is still available although the signal counts for Cal 2 decrease by 50%. Turning to the controls (PCU_1 with 1.25-1.79µ IU/ml and PCU_2 with 7.59-10.3µ IU/ml) that provide definite target ranges of TSH concentrations, these target ranges are fully met after addition of the label-specific binding partner.

TABLE 4

Immunoassay for detecting TSH (Lot 188368) - Reduction of Interference Reference Range 0.270-4.20 µIU/ml

| | Competitior Assay Result [µIU/mL] | TSH - Signal [Counts] | | TSH - Full-Calibration [µIU/ml] | | Interference |
|---|---|---|---|---|---|---|
| | | Reference (untreated) | Addition of 20 µg/mL Mab<BPRu>M-1 IgG in R2 | Reference (untreated) | Addition of 20 µg/mL Mab<BPRu>M-1 IgG in R2 | Reduction by Present Invention [%] |
| CAL1 | | 840 | 710 | | | |
| CAL2 | | 33176 | 16305 | | | |
| PCU_1 Target Value 1.52 µIU/ml (1.25-1.79) | | 27127 | 13946 | 1.53 | 1.64 | |

TABLE 4-continued

Immunoassay for detecting TSH (Lot 188368) - Reduction of Interference Reference Range 0.270-4.20 µIU/ml

| | | TSH - Signal [Counts] | | TSH - Full-Calibration [µIU/ml] | | Interference |
|---|---|---|---|---|---|---|
| | Competitior Assay Result [µIU/mL] | Reference (untreated) | Addition of 20 µg/mL Mab<BPRu>M-1 IgG in R2 | Reference (untreated) | Addition of 20 µg/mL Mab<BPRu>M-1 IgG in R2 | Reduction by Present Invention [%] |
| PCU_2 Target Value 8.93 µIU/ml (7.59-10.3) | | 157894 | 76401 | 9.06 | 9.11 | |
| Interfering Sample 1 | 0.020 | 349630 | 36961 | 20.2 | 4.41 | 78% |
| Interfering Sample 2 | 0.004 | 112294 | 5671 | 6.43 | 0.629 | 90% |
| Interfering Sample 3 | 0.010 | 143728 | 762 | 6.24 | 0.010 | 100% |
| Interfering Sample 4 | 0.660 | 617947 | 96776 | 36.2 | 11.5 | 69% |

As a next step, interfering samples 1 to 4 were measured without the addition of a label-specific binding partner these samples seemed to indicate a certain TSH concentration. These samples showed very high signals in the untreated TSH standard assay that—according to the medical history of these patients—did not fit into their individual medical picture of thyroid hormone analysis. However, when the label-specific binding partner according to the invention was added, the interference was reduced considerably so that 3 of the 4 samples were found in the correct TSH target ranges. For example, Interfering sample 3—when measured untreated—provided a signal of 143,728. Upon addition of the label-specific antibody, said interference could be reduced completely resulting in 782 counts which was very close to the Cal1 calibrator signal (100% interference reduction). The TSH concentrations of Interfering samples 1, 2 and 4, which were very high in the untreated measurement were reduced to a great extent by adding the label-specific binding partner resulting in a reduction of interference by 78%, 90% and 69%, respectively.

The invention claimed is:

1. An immunoassay method for detecting an analyte in an isolated sample suspected to contain said analyte comprising:
  incubating said sample with a plurality of binding partners, wherein one binding partner carries a detectable label and is capable of binding to the analyte and another binding partner is a label-specific binding partner that does not carry a label but binds to said detectable label, wherein the label-specific binding partner is a biological molecule based on a polypeptide composed of amino acids, wherein the incubating is maintained for a time period sufficient for allowing said analyte, if present in the sample, to bind with said binding partner carrying the detectable label thus forming an immunoreaction product; and
  detecting the presence of said immunoreaction product directly or indirectly via the detectable label.

2. An immunoassay method according to claim 1, comprising:
  a. incubating said sample with
    i. a first binding partner that binds to the analyte and that carries a detectable label;
    ii. a second binding partner that is capable of being bound to a solid phase and that binds to the analyte; and
    iii. a third binding partner that binds to said detectable label of said first binding partner, wherein said third binding partner does not carry a label, wherein said third binding partner is a biological molecule based on a polypeptide composed of amino acids;
  b. forming an immunoreaction admixture by admixing said sample with said first, second and third binding partners;
  c. maintaining said immunoreaction admixture for a time period sufficient for allowing said analyte if present in the body fluid sample to immunoreact with said first and second binding partners to form an immunoreaction product; and allowing said third binding partner to immunoreact with said detectable label of said first binding partner; and
  d. detecting at least one of the presence and the concentration of any of said immunoreaction product.

3. An immunoassay method according to claim 1, comprising:
  a. incubating said sample with
    i. a first binding partner that binds to the analyte and that does not carry a detectable label;
    ii. a specifier which binds to the first binding partner and which competes with the analyte for binding to the first binding partner wherein said specifier carries a detectable label;
    iii. a second binding partner that is capable of being bound to a solid phase and that binds to said first binding partner and which competes with said analyte and said specifier for binding to said first binding partner; and
    iv. a third binding partner that binds to said detectable label of said specifier, wherein said third binding partner does not carry a label, wherein said third binding partner is a biological molecule based on a polypeptide composed of amino acids;
  b. forming an immunoreaction admixture by admixing said sample with said first, second and third binding partners and said specifier;
  c. maintaining said immunoreaction admixture for a time period sufficient for allowing said analyte if present in said body fluid sample to compete with said specifier and second binding partner for binding to said first binding partner, and allowing said third binding partner to immunoreact with said detectable label of said specifier, thereby forming an immunoreaction product; and
  d. detecting at least one of the presence and the concentration of any of said immunoreaction product.

4. An immunoassay method according to claim 1 wherein said analyte is selected from the group consisting of a biological and a chemical molecule associated with at least one of an infection, an inflammatory, septic, metabolic, cardiac, and an oncologic event or disease.

5. An immunoassay method according to claim 4 wherein said analyte is selected from the group consisting of a hormone, an antigen and an antibody.

6. An immunoassay method according to claim 5 wherein said analyte is an antibody against a pathogen selected from the group consisting of
   a. a Toxoplasma organism;
   b. a hepatitis virus; and
   c. a herpes virus;
   d. rubella virus;
   e. a retrovirus;
   f. paramyxoviruses; and
   g. a Borrelia organism.

7. An immunoassay method according to claim 6 wherein said analyte is an antibody of the IgM class.

8. An immunoassay method according to claim 7 wherein said analyte is an antibody of the IgM class present as a reaction to an infection with a pathogen selected from the group consisting of Toxoplasma gondii, cytomegalovirus (CMV), Rubella, hepatitis A and hepatitis B.

9. An immunoassay method according to claim 1 wherein said detectable label is selected from the group consisting of an enzymatic, radioactive, luminescent, chemiluminescent and electrochemiluminescent label.

10. A reagent kit for detecting an analyte by an immunoassay comprising a plurality of binding partners wherein at least one of the binding partners binds to the analyte, and one of the binding partners carries a detectable label and one of the binding partners is label-specific and binds to said detectable label but does not carry a detectable label, wherein the label-specific binding partner is a biological molecule based on a polypeptide composed of amino acids.

11. An immunoassay method according to claim 6 wherein said a pathogen is Toxoplasma gondii.

12. An immunoassay method according to claim 6 wherein said a pathogen is a hepatitis virus selected from the group consisting of hepatitis A virus (HAV), hepatitis B virus (HBV) and hepatitis C virus (HCV).

13. An immunoassay method according to claim 6 wherein said pathogen is a herpes virus selected from the group consisting of human herpes simplex virus 1 and 2 (HHV1 and HHV2), varicella zoster virus (HHV3), Epstein-Barr virus (HHV4/EBV) or human cytomegalovirus (HHV5) and human herpes viruses 6, 7, and 8.

14. An immunoassay method according to claim 6 wherein said pathogen is a retrovirus selected from the group consisting of human immunodeficiency virus (HIV) 1 and 2 and human T-lymphotropic virus (HTLV) 1 and 2.

15. An immunoassay method according to claim 6 wherein said pathogen is a paramyxoviruses selected from the group consisting of measles virus and mumps virus.

* * * * *